(12) United States Patent
Layman et al.

(10) Patent No.: US 7,897,127 B2
(45) Date of Patent: Mar. 1, 2011

(54) COLLECTING PARTICLES FROM A FLUID STREAM VIA THERMOPHORESIS

(75) Inventors: Frederick P. Layman, Carefree, AZ (US); Maximilian A. Biberger, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 333 days.

(21) Appl. No.: 12/151,860

(22) Filed: May 9, 2008

(65) Prior Publication Data
US 2008/0277269 A1 Nov. 13, 2008

Related U.S. Application Data

(60) Provisional application No. 60/928,946, filed on May 11, 2007.

(51) Int. Cl.
B01D 45/00 (2006.01)
B01D 49/02 (2006.01)
B01J 19/00 (2006.01)

(52) U.S. Cl. .............. 423/215.5; 422/168; 422/173; 422/198; 422/200; 422/202

(58) Field of Classification Search ............ 423/215.5; 422/168, 173, 198, 200, 202
See application file for complete search history.

(56) References Cited

U.S. PATENT DOCUMENTS

| | | | |
|---|---|---|---|
| 2,419,042 A | 4/1947 | Todd | 202/205 |
| 2,519,531 A | 8/1950 | Worn | 230/95 |
| 2,562,753 A | 7/1951 | Trost | |
| 2,689,780 A | 9/1954 | Rice | 23/106 |
| 3,001,402 A | 9/1961 | Koblin | 73/421.5 |
| 3,067,025 A | 12/1962 | Chisholm | |
| 3,178,121 A | 4/1965 | Wallace, Jr. | |
| 3,401,465 A | 9/1968 | Larwill | |
| 3,457,788 A | 7/1969 | Miyajima | 73/422 |

(Continued)

FOREIGN PATENT DOCUMENTS

JP 56-146804 11/1981

(Continued)

OTHER PUBLICATIONS

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.

(Continued)

Primary Examiner—Timothy C Vanoy
(74) Attorney, Agent, or Firm—Haverstock & Owens, LLP

(57) ABSTRACT

A method of collecting particles from a gas-particle stream having a first temperature and a plurality of particles, the method comprising: cooling an interior surface of a collection chamber to a second temperature less than the first temperature of the gas-particle stream; flowing the gas-particle stream through the chamber, wherein the gas-particle stream is directed along the cooled interior surface of the collection chamber, and a temperature gradient between the gas-particle stream and the cooled interior surface creates a thermophoretic force; and the thermophoretic force attracting the particles from the gas-particle stream to the interior surface of the collection chamber, wherein the particles are deposited onto the interior surface of the collection chamber.

20 Claims, 9 Drawing Sheets

U.S. PATENT DOCUMENTS

| | | | |
|---|---|---|---|
| 3,537,513 A | 11/1970 | Austin et al. | 165/70 |
| 3,741,001 A | 6/1973 | Fletcher et al. | 73/28 |
| 3,774,442 A | 11/1973 | Gustavsson | 73/28 |
| 3,959,420 A | 5/1976 | Geddes et al. | 261/112 |
| 4,008,620 A | 2/1977 | Narato et al. | 73/421.5 A |
| 4,018,388 A | 4/1977 | Andrews | |
| 4,139,497 A | 2/1979 | Castor et al. | |
| 4,171,288 A | 10/1979 | Keith et al. | |
| 4,248,387 A | 2/1981 | Andrews | |
| 4,284,609 A * | 8/1981 | deVries | 423/243.08 |
| 4,388,274 A | 6/1983 | Rourke et al. | |
| 4,436,075 A | 3/1984 | Campbell et al. | 123/557 |
| 4,513,149 A | 4/1985 | Gray et al. | |
| 4,764,283 A | 8/1988 | Ashbrook et al. | |
| 4,824,624 A | 4/1989 | Palicka et al. | 264/67 |
| 4,855,505 A | 8/1989 | Koll | |
| 4,983,555 A | 1/1991 | Roy et al. | 501/120 |
| 4,987,033 A | 1/1991 | Abkowitz et al. | 428/469 |
| 5,043,548 A | 8/1991 | Whitney et al. | 219/121.84 |
| 5,073,193 A | 12/1991 | Chaklader et al. | 75/346 |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,439,865 A | 8/1995 | Abe et al. | |
| 5,485,941 A | 1/1996 | Guyomard et al. | 222/1 |
| 5,534,149 A | 7/1996 | Birkenbeil et al. | |
| 5,553,507 A | 9/1996 | Basch et al. | 73/863.01 |
| 5,611,896 A | 3/1997 | Swanepoel et al. | 204/169 |
| 5,630,322 A | 5/1997 | Heilmann et al. | 62/95 |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |
| 5,811,187 A | 9/1998 | Anderson et al. | 428/403 |
| 5,851,507 A | 12/1998 | Pirzada et al. | |
| 5,853,815 A | 12/1998 | Muehlberger | 427/446 |
| 5,905,000 A | 5/1999 | Yadav et al. | 429/33 |
| 5,935,293 A | 8/1999 | Detering et al. | 75/10.29 |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,012,647 A | 1/2000 | Ruta et al. | 239/132.1 |
| 6,033,781 A | 3/2000 | Brotzman, Jr. et al. | 428/405 |
| 6,059,853 A | 5/2000 | Coombs | 75/332 |
| 6,102,106 A | 8/2000 | Manning et al. | 165/76 |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,344,271 B1 | 2/2002 | Yadav et al. | 428/402 |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,413,781 B1 * | 7/2002 | Geis et al. | 436/178 |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,554,609 B2 | 4/2003 | Yadav et al. | 432/9 |
| 6,562,495 B2 | 5/2003 | Yadav et al. | 429/12 |
| 6,569,397 B1 | 5/2003 | Yadav et al. | 423/345 |
| 6,569,518 B2 | 5/2003 | Yadav et al. | 428/323 |
| 6,572,672 B2 | 6/2003 | Yadav et al. | 75/343 |
| 6,596,187 B2 | 7/2003 | Coll et al. | |
| 6,603,038 B1 | 8/2003 | Hagemeyer et al. | |
| 6,607,821 B2 | 8/2003 | Yadav et al. | 428/323 |
| 6,610,355 B2 | 8/2003 | Yadav et al. | 427/115 |
| 6,635,357 B2 | 10/2003 | Moxson et al. | 428/548 |
| 6,641,775 B2 | 11/2003 | Vigliotti et al. | 264/618 |
| 6,652,822 B2 | 11/2003 | Phillips et al. | 423/290 |
| 6,652,967 B2 | 11/2003 | Yadav et al. | 428/403 |
| 6,669,823 B1 | 12/2003 | Sarkas et al. | 204/164 |
| 6,682,002 B2 | 1/2004 | Kyotani | 239/318 |
| 6,689,192 B1 | 2/2004 | Phillips et al. | 75/342 |
| 6,699,398 B1 | 3/2004 | Kim | 216/55 |
| 6,706,097 B2 | 3/2004 | Zornes | 96/153 |
| 6,713,176 B2 | 3/2004 | Yadav et al. | 428/402 |
| 6,716,525 B1 | 4/2004 | Yadav et al. | 428/402 |
| 6,746,791 B2 | 6/2004 | Yadav et al. | 429/30 |
| 6,772,584 B2 | 8/2004 | Chun et al. | 60/275 |
| 6,786,950 B2 | 9/2004 | Yadav et al. | 75/346 |
| 6,813,931 B2 | 11/2004 | Yadav et al. | 73/31.05 |
| 6,817,388 B2 | 11/2004 | Tsangaris et al. | 141/82 |
| 6,832,735 B2 | 12/2004 | Yadav et al. | 241/16 |
| 6,838,072 B1 | 1/2005 | Kong et al. | 423/594.2 |
| 6,855,426 B2 | 2/2005 | Yadav | 428/403 |
| 6,855,749 B1 | 2/2005 | Yadav et al. | 523/105 |
| 6,886,545 B1 | 5/2005 | Holm | 123/568.21 |
| 6,896,958 B1 | 5/2005 | Cayton et al. | 428/323 |
| 6,902,699 B2 | 6/2005 | Fritzemeier et al. | 419/38 |
| 6,916,872 B2 | 7/2005 | Yadav et al. | 524/430 |
| 6,919,527 B2 | 7/2005 | Boulos et al. | 219/121.52 |
| 6,933,331 B2 | 8/2005 | Yadav et al. | 523/210 |
| 6,986,877 B2 | 1/2006 | Takikawa et al. | 423/447.3 |
| 6,994,837 B2 | 2/2006 | Boulos et al. | 423/613 |
| 7,007,872 B2 | 3/2006 | Yadav et al. | 241/1 |
| 7,052,777 B2 | 5/2006 | Brotzman, Jr. et al. | 428/570 |
| 7,073,559 B2 | 7/2006 | O'Larey et al. | 164/76.1 |
| 7,081,267 B2 | 7/2006 | Yadav | 427/115 |
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 7,494,527 B2 | 2/2009 | Jurewicz et al. | |
| 7,572,315 B2 | 8/2009 | Boulos et al. | |
| 7,615,097 B2 | 11/2009 | McKechnie et al. | |
| 7,622,693 B2 | 11/2009 | Foret | |
| 2001/0042802 A1 | 11/2001 | Youds | |
| 2002/0068026 A1 | 6/2002 | Murrell et al. | |
| 2002/0079620 A1 | 6/2002 | DuBuis et al. | 264/328.14 |
| 2003/0036786 A1 | 2/2003 | Duren et al. | 607/96 |
| 2003/0066800 A1 | 4/2003 | Saim et al. | |
| 2003/0108459 A1 | 6/2003 | Wu et al. | 422/186.04 |
| 2003/0223546 A1 | 12/2003 | McGregor et al. | 378/143 |
| 2004/0009118 A1 | 1/2004 | Phillips et al. | |
| 2004/0023453 A1 | 2/2004 | Xu et al. | |
| 2004/0103751 A1 | 6/2004 | Joseph et al. | 75/10.19 |
| 2004/0167009 A1 | 8/2004 | Kuntz et al. | 501/95.2 |
| 2004/0251017 A1 | 12/2004 | Pillion et al. | 165/289 |
| 2005/0000321 A1 | 1/2005 | O'Larey et al. | 75/952 |
| 2005/0000950 A1 | 1/2005 | Schroder et al. | 219/121.59 |
| 2005/0077034 A1 | 4/2005 | King | 165/163 |
| 2005/0097988 A1 | 5/2005 | Kodas et al. | 75/332 |
| 2005/0220695 A1 | 10/2005 | Abatzoglou et al. | |
| 2005/0233380 A1 | 10/2005 | Pesiri et al. | 435/7.1 |
| 2005/0240069 A1 | 10/2005 | Polverejan et al. | 585/444 |
| 2005/0258766 A1 | 11/2005 | Kim | 315/111.21 |
| 2006/0051505 A1 | 3/2006 | Kortshagen et al. | 427/212 |
| 2006/0068989 A1 | 3/2006 | Ninomiya et al. | |

| | | |
|---|---|---|
| 2006/0096393 A1 | 5/2006 | Pesiri .................... 73/863.21 |
| 2006/0105910 A1 | 5/2006 | Zhou et al. |
| 2006/0108332 A1 | 5/2006 | Belashchenko ........ 219/121.47 |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. ....... 422/151 |
| 2006/0231525 A1 | 10/2006 | Asakawa et al. ............. 216/56 |
| 2007/0063364 A1 | 3/2007 | Hsiao et al. .................... 264/5 |
| 2007/0084308 A1 | 4/2007 | Nakamura et al. ............ 75/346 |
| 2007/0084834 A1 | 4/2007 | Hanus et al. ............. 219/121.5 |
| 2007/0087934 A1 | 4/2007 | R.M. Martens et al. ..... 502/214 |
| 2007/0173403 A1 | 7/2007 | Koike et al. |
| 2007/0253874 A1 | 11/2007 | Foret |
| 2008/0105083 A1 | 5/2008 | Nakamura et al. |
| 2008/0277267 A1 | 11/2008 | Biberger et al. |

FOREIGN PATENT DOCUMENTS

| | | |
|---|---|---|
| WO | WO 02/092503 A1 | 11/2002 |
| WO | 2004052778 A2 | 6/2004 |
| WO | WO 2006/079213 A1 | 8/2006 |

OTHER PUBLICATIONS

J. Heberlein, "New Approaches in Thermal Plasma Technology", Pure Appl. Chem., vol. 74, No. 3, 2002, pp. 327-335.

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I li, P. Fauchais, Universite de Limoges, 123 Avenue A. Thomas 87000, Limoges, F., Pure & Chem, vol. 68, No. 5, pp. 1093-1099, 1996.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M.Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

Kenvin et al. "Supported Catalysts Prepared from Monuclear Copper Complexes: Catalytic Properties", Journal of Catalysis, pp. 81-91, vol. 135 (1992).

National Aeronautics and Space Administration, "Enthalpy", http://www.grc.nasa.gov/WWW/K-12/airplane/enthalpy.html, Nov. 23, 2009, 1 page.

* cited by examiner

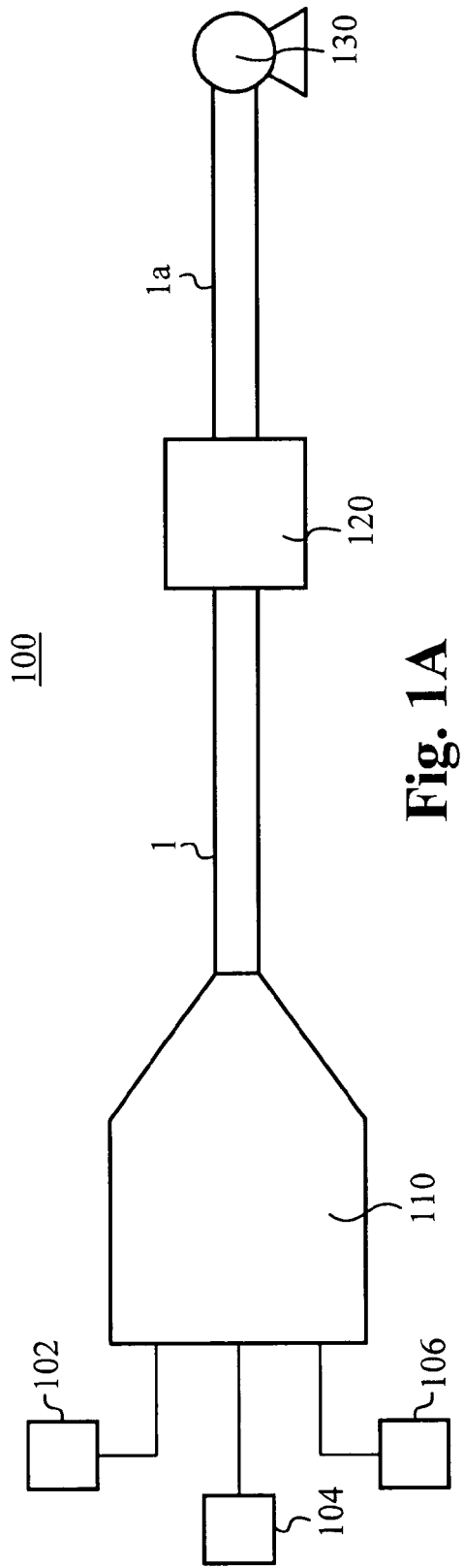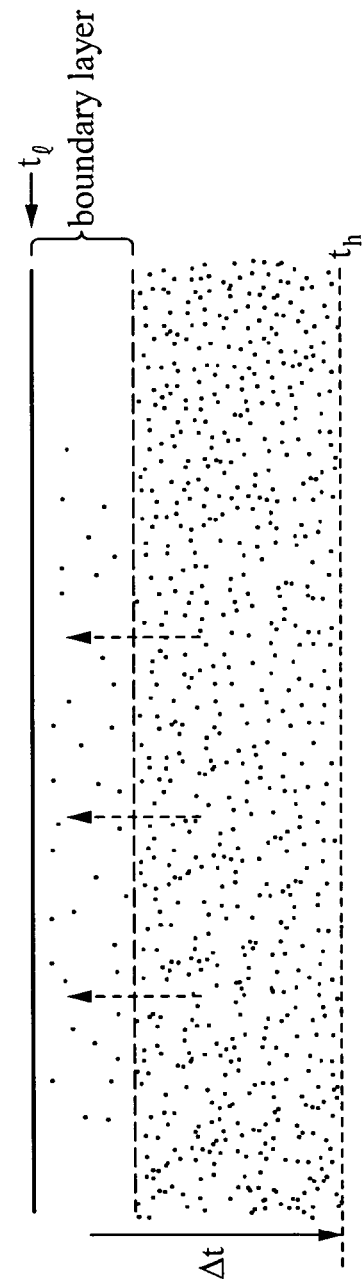
Fig. 1A
Fig. 1B

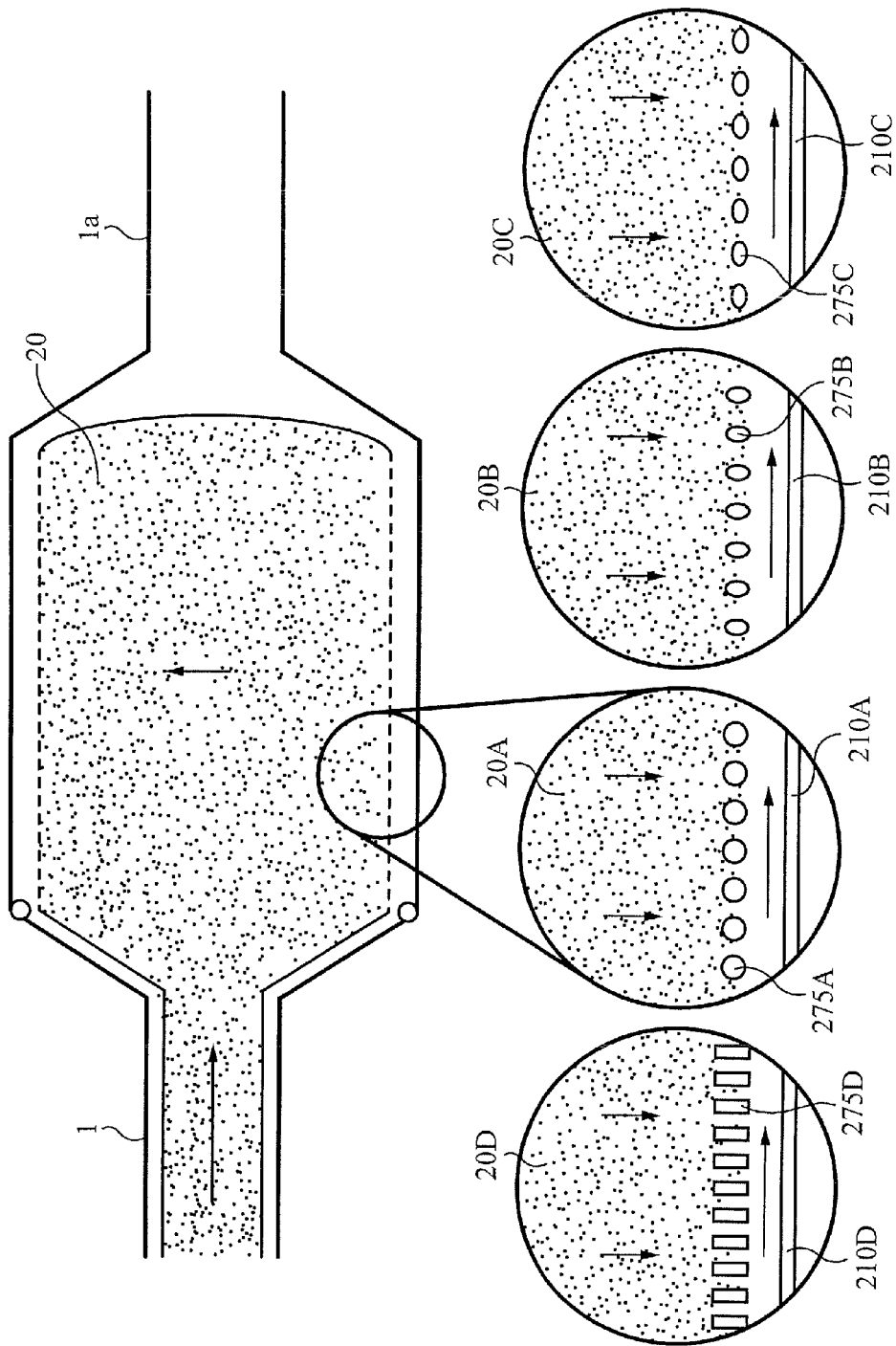

COLLECTING PARTICLES FROM A FLUID STREAM VIA THERMOPHORESIS

CROSS-REFERENCE TO RELATED APPLICATIONS

The present application claims priority to U.S. Provisional Application Ser. No. 60/928,946, filed May 11, 2007, entitled "MATERIAL PRODUCTION SYSTEM AND METHOD," which is hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE INVENTION

The present invention relates to systems and methods of collecting particles from a fluid stream via thermophoresis.

BACKGROUND OF THE INVENTION

The term thermophoresis refers to a phenomenon that occurs when a mixture of solid particles and fluid is exposed to a temperature gradient. The "thermophoretic force" that causes this phenomenon arises from interactions between fluid molecules and solid particles due to the temperature gradient. Because a fluid's temperature is a measure of the average velocity of that fluid's molecules, a temperature gradient within a fluid is essentially a gradient in average velocity and associated kinetic energy.

Higher temperature, faster moving fluid molecules collide more frequently, and at greater energy, with a particle than do lower temperature molecules. Thus, the temperature gradient produces an asymmetric interaction that tends to impart kinetic energy to the particle in the direction of lower temperature.

Past efforts have shown that thermophoresis plays a role in attracting particles from a hot gas mixture to a relatively cold surface. For example, in the case of a hot particle-gas mixture flowing within a cooler conduit, the conduit surfaces provide thermal boundary conditions that produce a sheath of colder gas surrounding the central core of the mixture. This thermal gradient produces a thermophoretic force that moves particles toward the conduit surfaces.

SUMMARY OF THE INVENTION

In one aspect of the present invention, a method of collecting particles from a gas-particle stream is provided. The gas-particle stream has a first temperature and a plurality of particles. The method comprising cooling an interior surface of a collection chamber to a second temperature less than the first temperature of the gas-particle stream. The gas-particle stream flows through the chamber and is directed along the cooled interior surface of the collection chamber. A temperature gradient between the gas-particle stream and the cooled interior surface creates a thermophoretic force. The thermophoretic force attracts the particles from the gas-particle stream to the interior surface of the collection chamber. The particles are deposited onto the interior surface of the collection chamber.

In another aspect of the present invention, a particle collector is provided. The particle collector comprises a conduit and a collection chamber fluidly coupled to the conduit via an inlet. The collection chamber has an interior surface thermally coupled to a fluid circulation structure. The fluid circulation structure is configured to cool the interior surface to a cooled temperature. The collection chamber is configured to receive a gas-particle stream from the conduit via the inlet. The gas-particle stream is received having a plurality of particles and having a temperature greater than the cooled temperature of the interior surface. The collection chamber is configured to flow the gas-particle stream through the chamber so that the gas-particle stream is directed along the cooled interior surface and a temperature gradient between the gas-particle stream and the cooled interior surface creates a thermophoretic force. The thermophoretic force attracts the particles from the gas-particle stream to the interior surface of the collection chamber. The particles are deposited onto the interior surface.

In some embodiments, the present invention provides a method of removing particles from a gas-particle stream having a first mean temperature and a mean velocity. The method comprises cooling a fluid channeling surface to a second mean temperature to form a cooled fluid channeling surface. The second mean temperature is lower than the first mean temperature. The gas-particle stream is decelerated to form a decelerated gas-particle stream. The decelerated gas-particle stream is directed through the cooled fluid channeling surface, thereby forming a temperature gradient between the decelerated gas-particle stream and the cooled fluid channeling surface sufficient to form a thermophoretic gradient within the gas-particle stream with enough strength to promote deposition of a proportion of the particles onto the cooled fluid channeling surface. In some embodiments, a boundary layer is formed along the cooled fluid-channeling surface. Thus, some embodiments of the present invention use a fluid-channeling surface as a thermophoretic deposition target.

Some embodiments of the present invention relate to thermophoretic particle collectors. In some of these embodiments, a thermophoretic particle collector comprises a deceleration structure having an axis, a first end and a second end, a channeling structure including a plurality of fluid cooling conduits and a matter transfer structure, a funnel structure, and a coolant circulation system configured to through the fluid cooling conduits of the channeling structure.

Preferably, the deceleration structure is configured to receive a primary matter stream having a first velocity vector substantially parallel with its axis through the inlet and divert the stream of matter into a plurality of secondary matter streams with velocity vectors substantially perpendicular to the axis. Most preferably, the first end of the deceleration structure includes an inlet configured to perform the preceding function. Also preferably, the fluid cooling conduits are separately sealed from the matter transfer structure but in thermal communication with the matter transfer structure and in fluid communication with a fluid port. In preferred embodiments, the matter transfer structure configured to receive the plurality of secondary matter streams from the deceleration structure and transfer the plurality of secondary matter streams through the channeling structure. The funnel structure preferably includes an outlet, and is configured to receive the plurality of secondary matter streams from the channeling structure, join the plurality of streams to form an output stream, and deliver the output stream to the outlet. Thus, some embodiments of the present invention use a matter transfer structure as a thermophoretic deposition target.

In some of these embodiments, a particle collector comprise a substantially cylindrical deceleration chamber having an axis, a first end, a second end, and an annular surface positioned a substantially fixed distance from the axis. The deceleration chamber is configured to receive a gas-particle stream traveling in an axial direction through the first end and redirect the gas-particle stream in a radial direction through a series of radial channels of the annular surface of the chamber. The annular surface comprises a series of circumferential channels sealed from the deceleration chamber and is configured to permit transport of a fluid therethrough. The radial channels are formed through the annular surface and each radial channel is adjacent to at least one circumferential channel. A substantially cylindrical funneling chamber having an axis, a first end, a second end, and an annular surface is positioned a substantially fixed distance from the axis. The funneling chamber is positioned coaxially with the deceleration chamber so that the funneling chamber is in fluid communication with the deceleration chamber through the radial channels. The first end of the funneling chamber is configured to interface with the first end of the deceleration chamber to form a seal, and the second end of the funneling chamber is configured to interface with a conduit. A coolant circulation system is configured to circulate coolant through the series of circumferential channels.

Some embodiments relate to a cylindrical thermophoretic particle collector having a major axis. A cylindrical thermophoretic particle collector in accordance with these embodiments comprises a first axially-directed end plate including a main inlet and a coolant port, a cylindrical inner body comprising a circumferential coolant-channeling structure, fluidly coupled to the coolant port of the first axially-directed end plate to permit circumferential circulation of coolant, that forms a plurality of radial channels in communication with an inner chamber of the inner body. An axially directed sealing plate is coupled to the circumferential coolant-channeling structure. A cylindrical outer body comprises a circumferential surface and is sealably coupled to the first axially-directed end plate. A second axially-directed end plate includes a main outlet and is sealably coupled to the cylindrical outer body.

Once particles have been collected on various deposition structures, they often must be removed therefrom and analyzed or used in some manner. Typically, the structures used for collection are removed from the collector under controlled conditions and the particles are detached therefrom via some combination of mechanical and thermal means. In some embodiments, the deposition surfaces are heated to produce a reverse thermophoretic effect, ejecting particles from the surfaces. In some embodiments, the deposition surfaces are vibrated to detach the particles. In some embodiments, the particles are scraped or otherwise mechanically removed from the deposition surfaces.

BRIEF DESCRIPTION OF THE DRAWINGS

FIG. 1A is a schematic illustration of one embodiment of a particle production system in which a thermophoretic particle collection system is included in accordance with the principles of the present invention.

FIG. 1B is a schematic illustration of thermophoretic effects during interactions between a collection of particles and a substrate.

FIG. 4A is a detailed view of one embodiment of a thermophoretic particle collector in accordance with the principles of the present invention.

FIG. 4B is a detailed view of another embodiment of a thermophoretic particle collector in accordance with the principles of the present invention.

FIG. 4C is a detailed view of yet another embodiment of a thermophoretic particle collector in accordance with the principles of the present invention.

FIG. 4D is a detailed view of yet another embodiment of a thermophoretic particle collector in accordance with the principles of the present invention.

DETAILED DESCRIPTION OF THE INVENTION

Figure 2A:
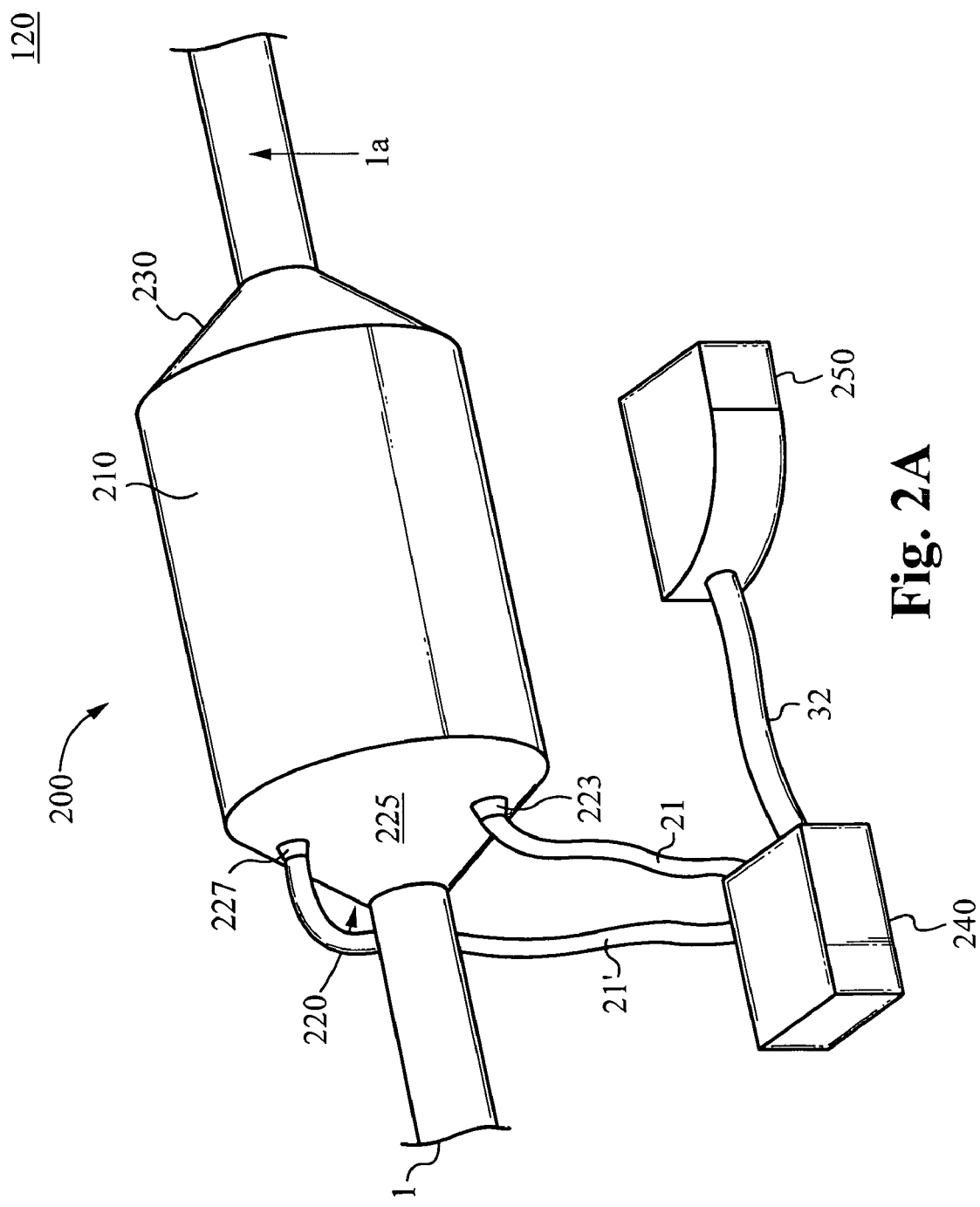
FIG. 2A illustrates one embodiment of a thermophoretic particle collection system in accordance with the principles of the present invention.

The description below concerns several embodiments of the invention. The discussion references the illustrated preferred embodiment. However, various modifications to the described embodiments will be readily apparent to those skilled in the art and the generic principles herein may be applied to other embodiments. Therefore, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders (nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accom- FIG. 1A illustrates a particle production system 100 including a thermophoretic particle collection system 120. The particle production system 100 comprises a reactor element 110, which is configured to produce a fluid stream comprising particles for collection. Reactor element 110 preferably includes several input ports and an output port. An energy supply 102, a working gas supply 104, and a precursor supply 106 can each be coupled to an input of the reactor element 110. The conduit section 1 fluidly couples the output port of the reactor element 110 to the thermophoretic particle collection system 120. The thermophoretic particle collection system 120 includes an input coupled to the conduit section 1 and an output coupled to a second conduit section 1a. The second conduit section 1a is also coupled to the suction-generating element 130.

The particle production system 100 takes a stream of gas from the working gas supply 104 into the reactor element 110 and delivers energy to the stream, thereby producing a plasma stream. Meanwhile, the suction generator 130 provides suction at the junction between the reactor 110 and the conduit section 1. The negative pressure stream of the suction motivates fluid within the reactor 110 into the conduit section 1, through the section and into the collection element 120, through the collection element 120 and into the second conduit section 1a, through that section and into the suction generator 130.

The suction produced by the generator 130 forces the plasma stream through the reactor 110 and toward the conduit section 1. Meanwhile, precursor material from the precursor supply 106 is introduced into the reactor element 110. The precursor material preferably vaporizes within the plasma stream. The resulting mixture of vapor and plasma cools within the reactor element 110 to form particles entrained in a stream of gas. This gas-particle stream is forced through the path outlined above.

As the gas-particle stream moves from the conduit section 1 through the collection element 120, particles are removed from the stream. Preferably, the collection element 120 is efficient enough to remove substantially all particles from the stream.

The collection systems 120 of the present invention operate to remove particles from a stream of gas by exploiting thermophoretic phenomena. Furthermore, these systems preferably operate to collect, consolidate, and isolate the removed particles. Preferably, these various operations occur during phases of operation. In some embodiments, some phases of operation overlap in time. In other embodiments, no phases of operation overlap in time.

FIG. 1B provides a schematic illustration of thermophoretic effects when a relatively high temperature collection of particles and gas is exposed to a relatively low temperature surface. The illustrated particle gas mixture is exposed to a high temperature boundary condition, $t_h$ and a low temperature boundary condition, $t_r$. Many physical situations produce boundary conditions similar to those illustrated. For example, configuring a heater within a cold-walled chamber and flowing a gas-particle mixture into the chamber, or a stream of hot gas-particle mixture flowing from a heated reactor into a cooled conduit. In the latter example, the $t_h$ boundary condition corresponds to the center of the stream, which is continually supplied with hot mixture from the reactor, such as reactor 110.

With respect to FIG. 1B, assume a cooled substrate provides the low temperature boundary, while the high temperature boundary is provided by a heater and occurs in free space. The boundary conditions produce a temperature gradient, ?t within the mixture, moving from low temperatures at the substrate to high temperatures at the other boundary. This temperature gradient produces a thermophoretic effect in the opposite direction, forcing particles toward the low temperature substrate.

Meanwhile, interactions between the substrate and the mixture produce multiple boundary layers of cooled, relatively less turbulent gas along the surface of the substrate. As particles are forced toward the substrate, they eventually enter a critical boundary layer, at which point deposition inevitably occurs. The thickness of the critical boundary layer varies depending on particle size. In thermophoretic systems with different configurations, other parameters will affect the formation of critical boundary layers for a given particle size. Some embodiments of the present invention seek to produce collectors in which a substantial proportion of particles of a selected size will pass through a critical boundary layer.

Referring now to FIG. 2A, a thermophoretic particle collection system 120 can comprise a collector 200, a heat rejection and coolant circulation element 240, and a power supply 250. Typically, the collector 200 is configured with a conduit system, comprising sections 1 and 1a, to receive a matter stream flowing within the conduit section 1, collect particles from the stream, and deliver the remainder of the stream to the conduit section 1a.

The collector 200 is preferably a cylindrical thermophoretic particle collector. The outer structure of the collector 200 includes the cylindrical body 210, which is coupled to a first axially directed end plate 220 and a second axially directed end plate 230. Preferably, the interfaces between the cylindrical body 210 and the axially directed end plates 220 and 230 are sealed. In some embodiments, the cylindrical body 210 and the end plates 220 and 230 are integrally formed.

Preferably, each axially directed end plate includes features, such as ports, that are configured to mate with a conduit structure. As shown, the first axially directed end plate 220 includes a main inlet coupled to the conduit section 1. Preferably, this coupling is sealed and permits delivery of a matter stream from the conduit section 1 into the collector 200. Similarly, the second axially directed end plate 230 includes a main outlet coupled to conduit section 1a. Preferably, this coupling is also sealed and permits delivery, following particle collection, of a remainder of a matter stream to the conduit section 1a.

In a preferred embodiment, the collector 200 also includes structures for decelerating a matter stream, and passing the decelerated matter stream through a cooled surface to produce a thermophoretic effect that aids particle collection. These structures and their functions are discussed in more detail below with reference to FIG. 2B. However, the fluid coolant delivery system is illustrated in FIG. 2A. In the collection system 120, the collection surfaces within the collector 200 can be cooled by coolant supplied from the heat rejection and coolant circulation element 240, which can be powered by power supply 250.

The first axially directed end plate 220 of the collector 200 includes the first coolant port 223 and the second coolant port 227 formed through its face 225. The first coolant port 223 is fluidly coupled through the coolant conduit 21 to the heat rejection and circulation element 240, while the second coolant port 227 is similarly coupled through the coolant conduit 21'. In some embodiments, the first coolant port 223 serves as an inlet, and the second coolant port 227 serves as an outlet. In other embodiments, these roles are reversed. In either case, the heat rejection and coolant circulation element 240 is configured to supply coolant at a first temperature through the inlet, receive relatively higher temperature coolant from the outlet, cool the coolant back to the first temperature through a heat rejection means, and recirculate the coolant through the inlet again. In some embodiments of the present invention, other types of coolant circulation systems are used.

In the collection system 120, the heat rejection and coolant circulation element 240 is coupled to the power supply 250 through the power delivery conduit 32. Preferably, the heat rejection and coolant circulation element 240 is configured to circulate coolant and dissipate heat at selectable rates. The power consumption of the element 240 varies based on its specific settings. Therefore, the power supply is preferably configured to deliver a rate of power to the element 240 sufficient to meet a dynamic power requirement.

Figure 2B:
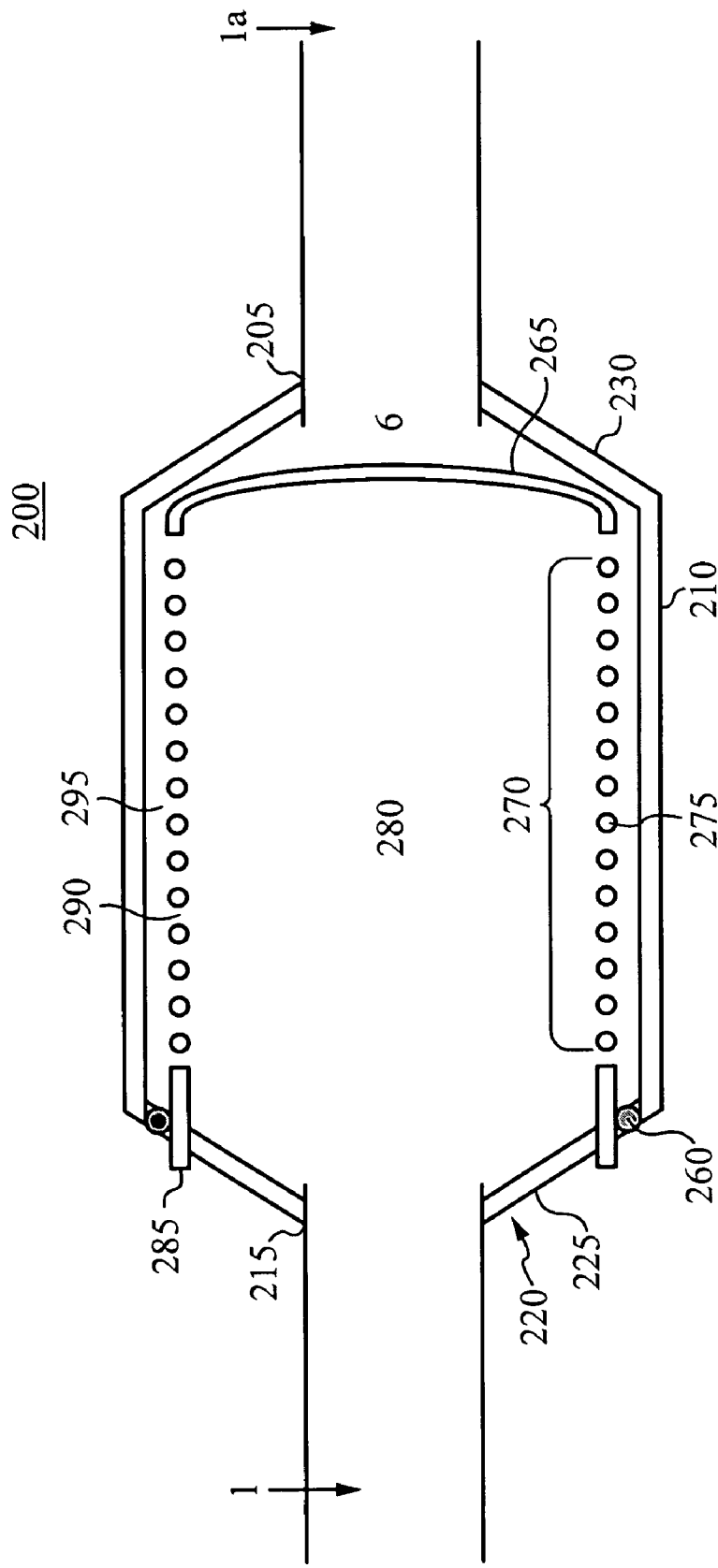
FIG. 2B is a cross-sectional view of one embodiment of a thermophoretic particle collector in accordance with the principles of the present invention.

Referring now to FIG. 2B, a particle collector 200 is coupled to the conduit sections 1 and 1a. The particle collector 200 comprises a cylindrical outer body 210, a first axially directed end plate 220, a second axially directed end plate 230, a cylindrical inner body 270, a sealing body 260, and an axially directed sealing plate 265.

The second axially directed end plate 230 includes the main outlet 205, which is coupled to the conduit section 1a. Together, the cylindrical outer body 210 and the second axially directed end plate 230 form a substantially cylindrical funneling chamber 6.

The funneling chamber 6 has an axis parallel with the axis of the conduits 1 and 1a, a first end distal from the main outlet 205, and a second end at the main outlet 205. The funneling chamber 6 has a cylindrical shape in the region of the cylindrical outer body 210, where the cylindrical outer body 210 forms a radially directed surface of the inner chamber, but narrows to meet the main outlet 205. The narrowing occurs in the region of the second axially directed end plate 230. In the illustrated embodiment, the faces of the second axially directed end plate 230 are not completely axially directed, but instead form an angle with the axis of the chamber, so as to gradually narrow the funneling chamber 6. This configuration is preferred. In some embodiments, the inner surface of the funneling chamber 6 forms a curve as it narrows to meet the main outlet 205.

In the illustrated embodiment, the cylindrical outer body 210 is integrally formed with the second axially directed end plate 230. In some embodiments, a cylindrical outer body 210 is coupled to an axially directed end plate. Preferably, the coupling between the cylindrical outer body 210 and the axially directed end plate can be sealed.

The first axially directed end plate 220 comprises the face 225 with a main inlet 215 formed therein. The main inlet 215 is coupled with the conduit section 1. Together, the first axially directed end plate 220, the cylindrical inner body 270, and the axially directed sealing plate 265 form a substantially cylindrical deceleration chamber 280. Preferably, the couplings between the sealing plate 265, the cylindrical inner body 270, and the first axially directed end plate 220 are sealed.

The deceleration chamber 280 has an axis parallel with that of the funneling chamber 6, a first end at the main inlet 215, and a second end at the sealing plate 265. The deceleration chamber 280 widens from the main inlet 215 at its first end into the region of the cylindrical inner body 270, which forms a radially directed surface of the deceleration chamber 270. In the illustrated embodiment, the face 225 is a frusto-conical body, which permits a gradual widening of the deceleration chamber 280. In some embodiments, the widening is more abrupt. In some embodiments, the widening of the deceleration chamber is more gradual. In some embodiments, the widening occurs along a curved path. The sealing plate 265 provides a curved surface at the second end of the deceleration chamber 280. In some embodiments, the surface of the sealing plate is not curved.

The deceleration chamber 280 and the funneling chamber 6 are coupled with one another in a fixed position. This coupling occurs through the sealing body 260. In some embodiments, the sealing body is an o-ring. The coupling produces a narrowed channel 295, shaped like a cylindrical shell, between a radially directed outer surface of the cylindrical inner body 270 and the radially directed surface of the funneling chamber 6.

The cylindrical inner body 270 comprises a series of circumferential conduits 275, which form a series of radial channels 290 between its inner and outer radially directed surfaces. Thus, in the assembled collector, the radial channels 290 provide fluid communication between the deceleration chamber 280 and the narrowed channel 295.

Preferably, the circumferential conduits 275 are coupled to coolant ports. Preferably, these conduits provide a closed loop for coolant to flow along the radially directed surface of the inner chamber. In some embodiments, coolant ports are located on the annular edge 285 of the inner cylindrical body 270, permitting delivery of coolant from outside the collector into the circumferential conduits 275. In some embodiments, coolant ports are located on the first axially directed plate 220 and configured to interface with the cylindrical inner body to permit delivery of coolant through the circumferential conduits 275.

Figure 3:
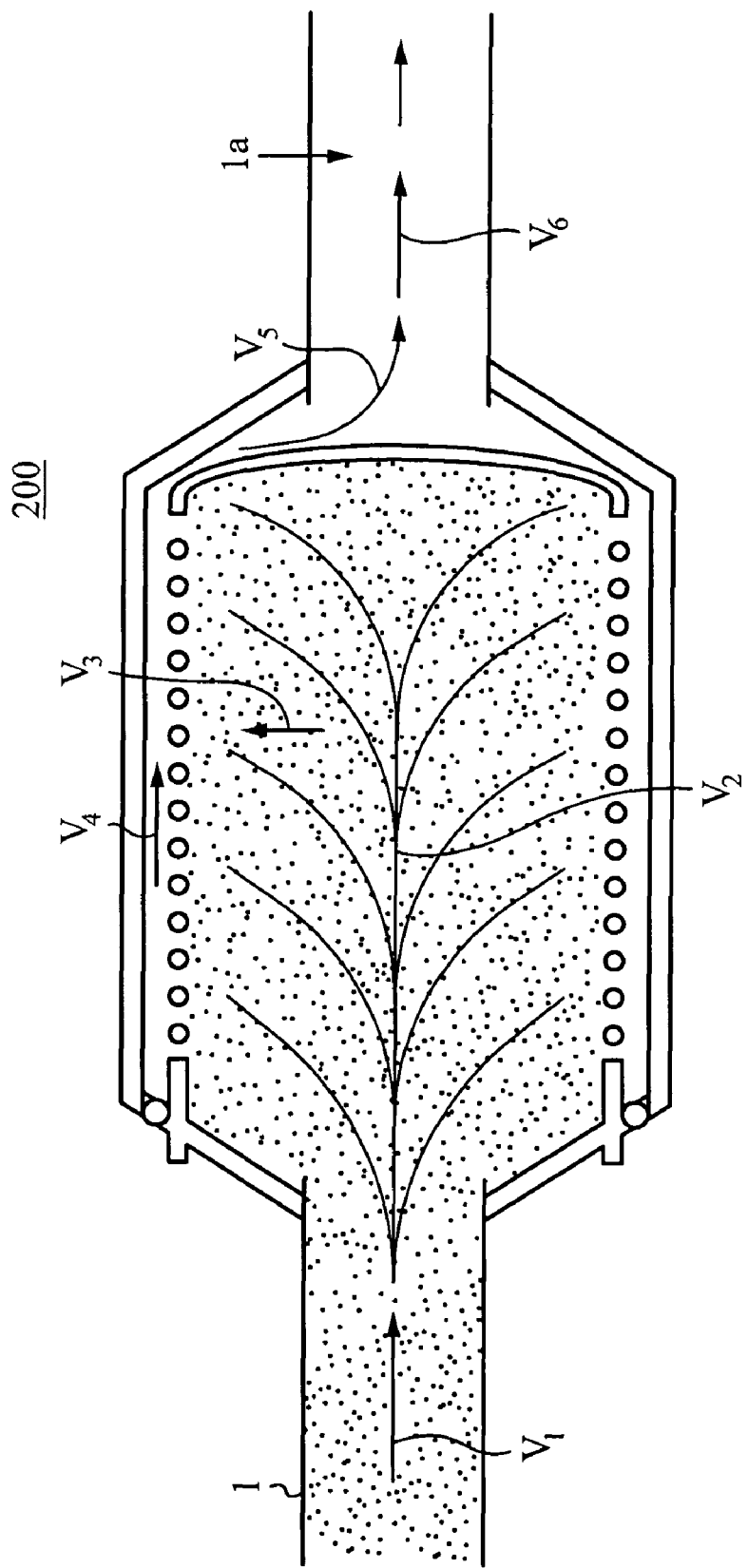
FIG. 3 is a cross-sectional view of one embodiment of a thermophoretic particle collector in operation in accordance with the principles of the present invention.

Referring now to FIG. 3, collector 200 is shown in operation. A gas-particle mixture travels at velocity $V_1$ along an axial direction through the conduit section 1 and into the deceleration chamber of the collector 200. As the gas particle mixture moves into the deceleration chamber, its trajectory changes. The mixture expands and decelerates, forced along various turbulent trajectories $V_2$, but generally traveling in a radial direction $V_3$. The specific magnitude of deceleration depends on parameters of the mixture, such as its entry velocity, pressure, and temperature, as well as physical characteristics of the collector, such as its diameter, volume, and the spacing and configuration of its channeling structure. Preferably, the magnitude of $V_2$ is at most ⅟20 of the magnitude of $V_1$. Furthermore, the magnitude of $V_3$ is preferably at most ⅟30 of the magnitude of $V_1$.

Eventually, the gas particle mixture flows into the radial channels of the cylindrical inner cylinder (see FIG. 2B and associated discussion) on its way toward the funneling chamber. As the gas particle mixture flows through the radial channels, the cooled surfaces of the channels produce a thermophoretic effect. The surfaces of each channel provide a low temperature boundary condition, while the continual supply of hot gas-particle mixture from the deceleration chamber provides a high temperature boundary condition. The resulting temperature gradient within the mixture forces particles toward the surfaces of the radial channels. A proportion of the particles so forced deposit on the surfaces, while the gas and any remaining particles continue through the channel. Preferably, substantially all particles within a target size range are collected.

In some embodiments of the present invention, the temperature gradient is controlled to be sufficient to produce a critical boundary layer within each radial channel for a selected particle size threshold. The deceleration of the particle-gas mixture assists in formation of the critical boundary layer. Thus, some embodiments promote particle deposition through manipulation of the boundary layers formed under thermophoretic conditions.

The gas and remaining particles flow from the deceleration chamber to the funneling chamber. This mixture flows axially along the surface of the funneling chamber at trajectory $V_4$. As the mixture flows through the narrowing portion of the chamber it begins to accelerate $V_5$. Once the mixture enters the conduit section $1a$ it again travels in an axial direction, this time at velocity $V_6$.

Once particles have been collected on various structures, they often must be removed therefrom and analyzed or used in some manner. Typically, the structures used for collection are removed from the collector under controlled conditions and the particles are detached therefrom via some combination of mechanical and thermal means. In some embodiments, the deposition surfaces are heated to produce a reverse thermophoretic effect, ejecting particles from the surfaces. In some embodiments, the deposition surfaces are vibrated to detach the particles. In some embodiments, the particles are scraped or otherwise mechanically removed from the deposition surfaces.

The embodiments of the present invention include many different types of channeling structures and radial channels configured to provide cooled deposition surfaces. A few examples of channeling configurations are illustrated in FIGS. 4A, 4B, 4C, and 4D. However, it is contemplated that other configurations can be used as well.

FIG. 4A illustrates a configuration of a particle collector in which spaced apart circular cross-sectioned circumferential conduits 275A provide a channeling structure between a deceleration chamber and a funneling structure. A mixture comprising gas and particles 20A within the deceleration structure moves through the spaces between the conduits 275A towards the cylindrical shell 210A of the funneling structure. Coolant flowing through the conduits 275A cools their outer surfaces. The cooled outer surfaces of the conduits 275A form a thermophoretic effect with the relatively hot gas particle mixture, encouraging the particles 20A to deposit on the conduits 275A. Preferably, the flow rate of the mixture in FIG. 4A is sufficiently low to permit a critical boundary layer to form over at least a portion of the surface of the conduit 275A for deposition of the particle 20A. As the particles 20A are deposited, remaining particles and gas flow out through the spaces between the conduits toward the cylindrical shell 210A and then flow parallel to the shell toward the outlet of the funneling chamber as illustrated.

FIG. 4B illustrates a configuration of a particle collector in which spaced apart oval cross-sectioned circumferential conduits 275B provide a channeling structure between a deceleration chamber and a funneling structure. A mixture comprising gas and particles 20B within the deceleration structure moves through the spaces between the conduits 275B toward the cylindrical shell 210B of the funneling structure. Coolant flowing through the conduits 275B cools their outer surfaces. The cooled outer surfaces of the conduits form a thermophoretic effect with the relatively hot gas particle mixture, encouraging the particles 20B to deposit on the conduits 275B. Preferably, the flow rate of the mixture in FIG. 4B is sufficiently low to permit a critical boundary layer to form over at least a portion of the surface of the conduit 275B for deposition of the particle 20B. As illustrated, the major axis of the oval conduits 275B is substantially parallel with the flow of the particle gas mixture out of the deceleration chamber. Embodiments with this configuration promote boundary layer formation within the radial channels between the conduits 275B. As the particles 20B are deposited, remaining particles and gas flow out through the spaces between the conduits toward the cylindrical shell 210B and then flow parallel to the shell toward the outlet of the funneling chamber as illustrated.

FIG. 4C illustrates a configuration of a particle collector in which spaced apart oval cross-sectioned circumferential conduits 275C provide a channeling structure between a deceleration chamber and a funneling structure. A mixture comprising gas and particles 20C within the deceleration structure moves through the spaces between the conduits 275C toward the cylindrical shell 210C of the funneling structure. Coolant flowing through the conduits 275C cools their outer surfaces. The cooled outer surfaces of the conduits form a thermophoretic effect with the relatively hot gas particle mixture, encouraging the particles 20C to deposit on the conduits 275 C. Preferably, the flow rate of the mixture in FIG. 4C is sufficiently low to permit a critical boundary layer to form over at least a portion of the surface of the conduit 275C for deposition of the particle 20C. As illustrated, the major axis of the oval conduits 275C is substantially perpendicular with the flow of the particle gas mixture out of the deceleration chamber. Embodiments with this configuration promote boundary layer formation along the surfaces of the conduits 275C that face the interior of the deceleration chamber. As the particles 20C are deposited, remaining particles and gas flow out through the spaces between the conduits toward the cylindrical shell 210C and then flow parallel to the shell toward the outlet of the funneling chamber as illustrated.

FIG. 4D illustrates a configuration of a particle collector in which spaced apart rectangular cross-sectioned circumferential conduits 275D provide a channeling structure between a deceleration chamber and a funneling structure. A mixture comprising gas and particles 20D within the deceleration structure moves through the spaces between the conduits 275D toward the cylindrical shell 210D of the funneling structure. Coolant flowing through the conduits 275D cools their outer surfaces. The cooled outer surfaces of the conduits form a thermophoretic effect with the relatively hot gas particle mixture, encouraging the particles 20D to deposit on the conduits 275D. Preferably, the flow rate of the mixture in FIG. 4D is sufficiently low to permit a critical boundary layer to form over at least a portion of the surface of the conduit 275D for deposition of the particle 20D. As illustrated, the long axis of the rectangular conduits 275D is substantially parallel with the flow of the particle gas mixture out of the deceleration chamber. Embodiments with this configuration promote boundary layer formation within the radial channels between the conduits 275D. As the particles 20D are deposited, remaining particles and gas flow out through the spaces between the conduits toward the cylindrical shell 210D and then flow parallel to the shell toward the outlet of the funneling chamber as illustrated.

Figure 5A:
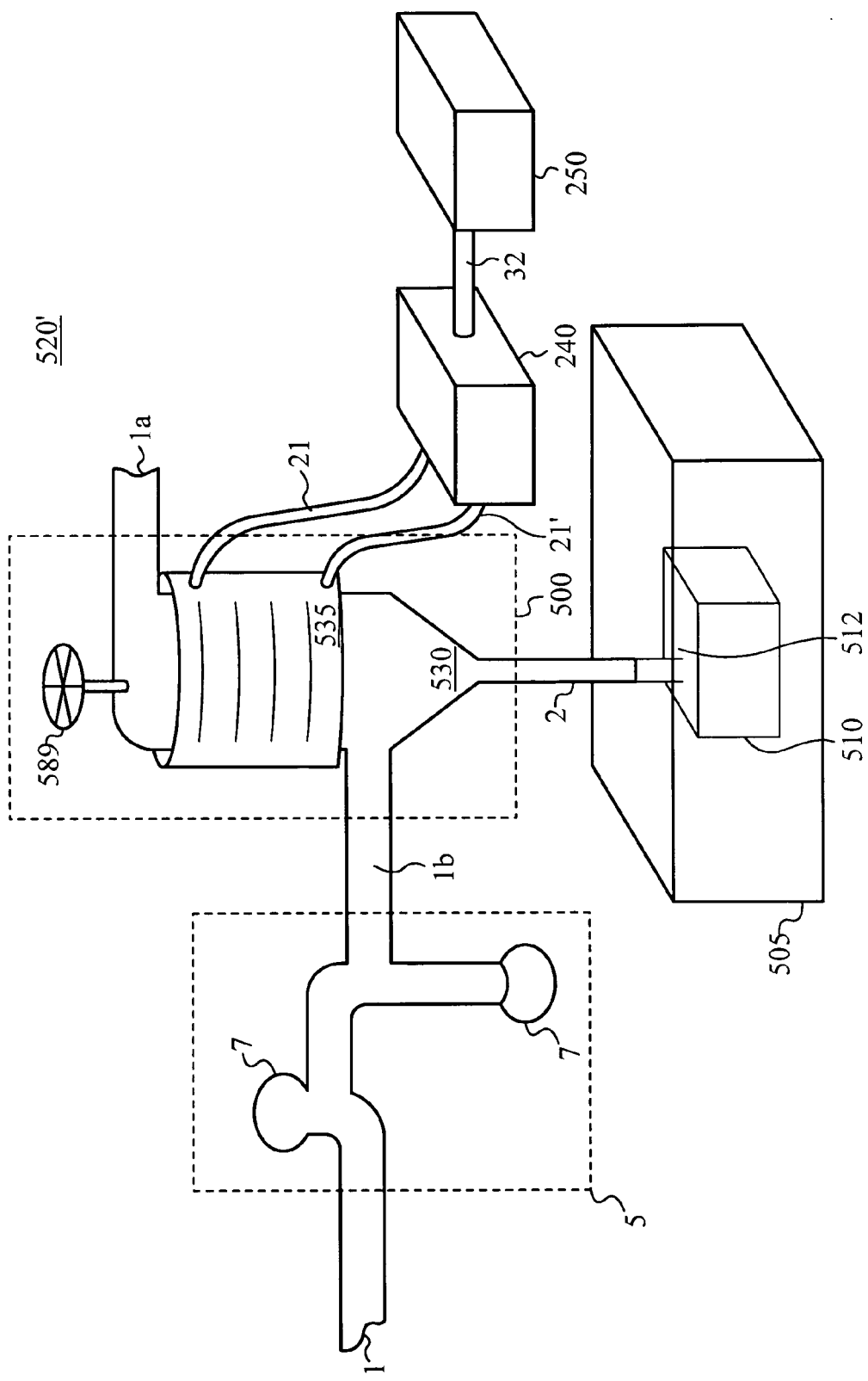
FIG. 5A illustrates another embodiment of a thermophoretic particle collection system in accordance with the principles of the present invention.

Referring now to FIG. 5A, a thermophoretic particle collection system 520' comprises a collector 500, the heat rejection and coolant circulation element 240, and the power supply 250. Typically, the collector 500 is configured with a conduit system, comprising sections $1b$ and $1a$, to receive a matter stream flowing within the conduit section $1b$, collect particles from the stream, and deliver the remainder of the stream to the conduit section $1a$.

The collector 500 is a cylindrical thermophoretic particle collector with an integrated particle removal mechanism. The outer structure of the collector 500 preferably includes the main body, which comprises a cylindrical chamber 570 (shown in FIGS. 5B-C), a consolidation outlet chamber 530, and an upper collection chamber.

Furthermore, the collector 500 preferably includes the fluid circulation structure 535, which is coupled to the main body, in thermal contact with an outer surface of the cylindrical chamber 570. Additionally, the collector 500 can include a particle removal actuator 589, which can be coupled to the main body. The actuator 589 is further coupled to an internal particle removal means, discussed in further detail below. The collector 500 further includes the consolidation chamber 505, which is coupled to the consolidation outlet chamber 530.

Figures 5B, 5C:
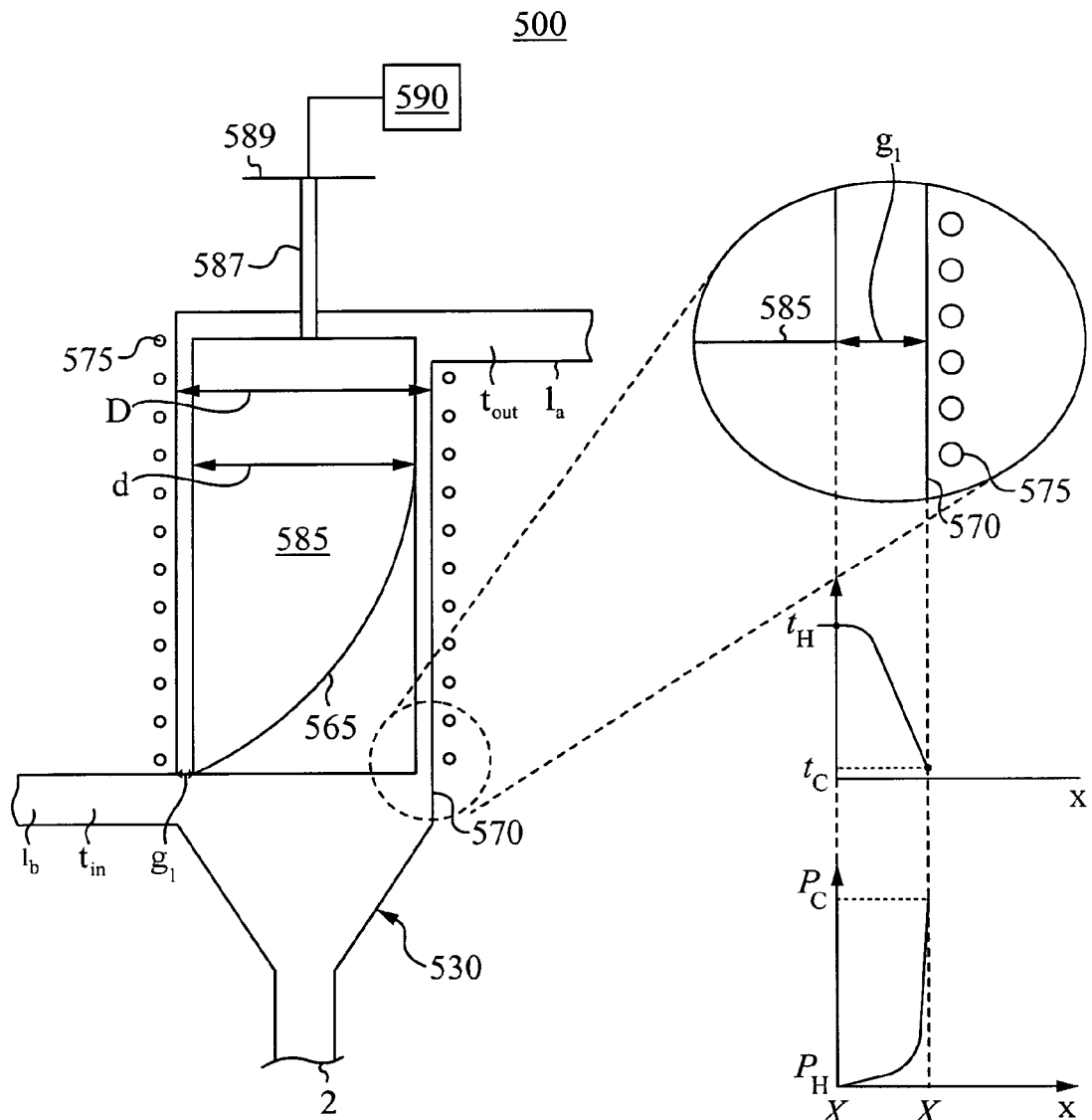
FIG. 5B is a cross-sectional view of one embodiment of a thermophoretic particle collector in accordance with the principles of the present invention.
FIG. 5C illustrate a graph of the idealized temperature and material distributions during particle deposition with respect to a cross-sectional view of a portion of a thermophoretic particle collector in accordance with the principles of the present invention.

The inner structure of the collector 500, as illustrated in FIG. 5B, includes the internal cylindrical body 585. Although in the illustrated embodiment the body 585 is cylindrical, in some embodiments the body is only substantially cylindrical. In other embodiments the body has a non-cylindrical shape.

Along with the main body, the internal cylindrical body 585 forms a channeling structure. In particular, portions of both the cylindrical chamber 570 of the main body and the internal cylindrical body 585 act as fluid channeling surfaces, forming a channel therebetween. Preferably, the fluid channeling structure is formed between a radially-directed inner surface of the cylindrical chamber 570 and an opposing, radially-directed outer surface of the internal cylindrical body 585.

Preferably, as illustrated, the channel has a substantially annular cross-section. The inner diameter of the annulus is determined by the diameter d of the internal cylindrical body 585, while the outer diameter is determined by the diameter D of the cylindrical chamber 570 of the main body. In the preferred configuration where the internal cylindrical body 585 and the cylindrical chamber 570 are coaxially disposed relative to one another, the radial distance $g_1$, the distance between the inner surface of the cylindrical chamber 570 and the outer surface of the internal cylindrical body 585, is equal to half the difference between D and d.

The channel formed between the internal cylindrical body 585 and the cylindrical chamber 570 fluidly couples the consolidation outlet chamber 530 with the upper collection chamber. In the illustrated configuration, the consolidation outlet chamber 530 acts as a supply chamber and distributes gas-particle mixture into the channel, while the upper chamber acts as funneling chamber and collects the output from the channel.

The conduit section 1b is in fluid communication with the consolidation outlet chamber 530. Preferably, the conduit section 1b is adjacent to the consolidation outlet chamber 530. Additionally, the consolidation outlet chamber 530 communicates fluidly with the cylindrical chamber 570. Preferably, these two chambers are adjacent. Furthermore, the cylindrical chamber 570 fluidly communicates with the upper collection chamber. However, these two chambers are preferably adjacent. The upper collection chamber fluidly communicates with the conduit section 1b. In preferred embodiments, these elements are preferably adjacent. Furthermore, in the preferred embodiments, the fluid communications set forth in this paragraph provide a connection from the conduit section 1a, through the consolidation outlet chamber 530, the cylindrical chamber 570, and the upper collection chamber to the conduit section 1b.

In the collector 500, a collection surface of the internal surface of the cylindrical chamber 570 is cooled by coolant supplied from the heat rejection and coolant circulation element 240. The fluid circulation structure 535 includes a plurality of fluid circulation channels (e.g., 575 of FIG. 5B). Each channel 575 is configured to circulate fluid through a path in thermal contact with the main body. The coolant circulation structure 535 includes fluid ports coupled to the fluid conduits 21 and 21'. In some embodiments, the first fluid conduit 21 supplies an inlet and the second fluid conduit 21' supplies an outlet. In other embodiments, these roles are reversed. In either case, the heat rejection and coolant circulation element 240 is configured to supply coolant at a first temperature to an inlet, receive relatively higher temperature coolant an outlet, cool the coolant back to the first temperature through a heat rejection means, and recirculate the coolant through the inlet again. In some embodiments, other types of coolant circulation systems are used.

To achieve this, the coolant circulation element 240 is fluidly coupled to the circulation structure 535 through the fluid conduits 21 and 21'. Preferably, channels and fluid circulators (not shown) within the fluid circulation element 240, the fluid circulation conduits 21 and 21', and the fluid circulation structure 535 together form a closed-loop cooling system. Also, the fluid circulation element 240 preferably includes a heat rejection element in thermal contact with the fluid channels or fluid circulators within the fluid circulation element 240.

In the collection system 520' in FIG. 5A, the heat rejection and coolant circulation element 240 is coupled to the power supply 250 through the power delivery conduit 32. Preferably, the heat rejection and coolant circulation element 240 is configured to circulate coolant and dissipate heat at selectable rates. The power consumption of the element 240 varies based on its specific settings. Therefore, the power supply is preferable configured to deliver a rate of power to the element 240 sufficient to meet a dynamic power requirement.

Referring to FIGS. 5A-B, the system 520' includes a particle removal means 565. In a preferred embodiment, the particle removal means 565 is a scraper rotatably coupled to the main body and configured to scrape the collection surface of the cylindrical body 570 when rotated.

In particular, the scraper 565 is coupled and disposed in a helical formation around the internal cylindrical body 585, which is coupled to the particle removal actuator 589. The configuration of the scraper 565 is such that the distance between it and the collection surface of the cylindrical chamber 570 is sufficiently small to permit the scraper 565 to remove material from the surface during rotation. In some embodiments, the scraper 565 and the internal surface are in contact, but not connected. Preferably, the scraper 565 substantially spans the distance g, between the outer surface of the internal cylindrical body 585 and the inner surface of the cylindrical chamber 570.

The particle removal actuator 589 and the internal cylindrical body 585 can be coupled to one another via the drive shaft 587. In the illustrated embodiment, the drive shaft 587 passes through the upper collection chamber, and is relatively narrow in diameter relative to the chamber. This arrangement permits the upper collection chamber to effectively collect output from the channel between the internal cylindrical body 585 and the cylindrical chamber 570.

Furthermore, the particle removal actuator 589 can be coupled to a particle removal control system 590. In various embodiments, the particle removal control system 590 takes on a variety of specific arrangements. For example, in some embodiments the particle removal control system 590 is a human and the particle removal actuator 589 is a manually operated wheel. In other embodiments, the particle removal control system 590 is an automated controller and the particle removal actuator 589 is a motor, or other automated actuator.

The collection system 520' can further include the consolidation chamber 505. The consolidation chamber 505 preferably includes an outer chamber 512 and an inner airlock 510. Preferably, the inner airlock 510 is disposed within the outer chamber 512, forming two chambers, one within the inner airlock 512 and one defined by the space left within the outer chamber 512 by the inner airlock 510. Preferably, the outer chamber 512 and the inner airlock 510 are sealably coupled, permitting airtight separation of the two chambers.

The consolidation outlet chamber 530 of the main body is fluidly coupled through the consolidation conduit 2 to the consolidation chamber 505. Specifically, the inner airlock 510 is coupled to the consolidation conduit 2, which is sealed from the outer chamber 512. The coupling between the consolidation conduit 2 and the inner airlock 510 is sealable, permitting optional fluid communication between the conduit 2 and the chamber within the inner airlock 510. Thus, by controlling the sealable couplings between the inner airlock 510 and both the conduit 2 and the outer chamber 512, a user optionally permits fluid communication between the inner airlock 510 and the conduit 2 or the inner airlock 510 and the outer chamber 512. Additionally, but permitting fluid communication in both of these cases, a user allows the conduit 2 and the outer chamber 512 to fluidly communicate. However, the operation of the sealable couplings preferably permits fluid communication between the inner airlock 510 and the conduit 2 while sealed from the outer chamber 512. Additionally, though not simultaneously, the operation of the sealable couplings preferably permits fluid communication between the inner airlock 510 and the outer chamber 512 while both are sealed from the conduit 2.

The collection system 520' can further include the classifier 5 fluidly coupled between the conduit section 1b and the conduit section 1. The classifier 5 is preferably positioned upstream from the collector 500 and is configured to remove particles above a certain size and/or mass threshold from the gas-particle stream prior to the stream reaching the collector 500.

The classifier 5 includes features configured to receive a gas-particle stream and to force changes in the stream's flow direction. More massive particles with greater inertia tend to be less responsive to these directional changes. The classifier 5 includes additional features configured to separate less responsive particles from the gas-particle stream. For example, in the illustrated classifier 5, the multiple curves with adjacent dead-ends 7 cause directional changes and separate low-response particles. More massive particles overshoot the curves, entering a dead-end 7 and becoming caught therein.

FIGS. 5B and 5C provide a schematic illustration of the internal structure of a collector 500. Additionally, FIG. 5C includes graphs illustrating idealized temperature and material distributions during the deposition phase of operation.

During deposition, the collector 500 receives a particle-gas mixture from the conduit section $1_b$ at input temperature $t_{in}$. The particle-gas mixture moves through the main body of the collector, where particles are deposited. The remainder of the mixture exits the main body, into the conduit section $1_a$. The output temperature $t_{out}$ is typically different than the input temperature.

The particle-gas mixture moves into the main body of the collector through the consolidation outlet chamber 530. Then, the mixture moves into the channel between the cylindrical chamber 570 and the internal cylindrical body 585. The channel, which has width $g_I$, comprises portions of the outer, radially-directed surface of the internal cylindrical body 585, as well as the inner, radially-directed surface of the cylindrical chamber 570.

Additionally, the scraper 565, which is coupled to the internal cylindrical body 585, is typically disposed to at least partially affect the path fluid takes through the channel. In the illustrated embodiment, the helical arrangement of the scraper 565 on the internal cylindrical body 585 biases the gas-particle mixture to flowing through the channel along a helical path.

Furthermore, the width of the channel is preferably configured to permit the channel to induce turbulence within the gas-particle mixture as it passes therethrough. Preferably, this turbulence is sufficiently high to result in highly efficient heat exchange between the collection surface and the gas-particle mixture. Additionally, the surface area of the channel is preferably matched to the surface area of the input conduit section $1_b$.

Meanwhile, a fluid circulation system supplies cooled coolant to the fluid circulation channels 575, which are in thermal contact with the main body. Specifically, the channels 575 are configured to transfer heat from a portion of the cylindrical chamber 570 when cooler fluid is passed therethrough. Thus, at least a portion of the inner surface of the cylindrical chamber 570 is cooled during the deposition phase. The temperature $t_C$ to which the surface is cooled is preferably lower than $t_{in}$. The surface that is cooled to $t_C$ is referred to as the collection surface.

On the other hand, the internal cylindrical body 585 is not cooled. During deposition, the temperature $t_H$ of the outer surface of the internal cylindrical body 585 is greater than $t_C$. Additionally, in some embodiments the internal cylindrical body 585 is heated. Preferably, the heating is performed by a controllable heating element (not shown). Furthermore, a controller integrated with the controller 590 preferably controls the heating element.

Thus, as the gas-particle mixture flows through the channel, it flows between two surfaces, one of temperature $t_H$, and one of temperature $t_C$. Preferably, the temperature of the mixture is greater than $t_C$, and falls between $t_H$ and $t_C$. In this situation, the temperature gradient between the internal cylindrical body 585 and the collection surface of the cylindrical chamber 570 is similar to that illustrated in FIG. 5C.

As shown, the temperature as a function of distance x from the body 585 begins at $t_H$, plateaus briefly, then decreases before asymptotically approaching $t_c$ as x approaches $g_1$. This temperature gradient away from the collection surface produces a thermophoretic force in the opposite direction, urging particles within the mixture toward the surface. This results in a particle density gradient, illustrated in the lower portion of FIG. 5C, where the particle density $P_H$ approaches zero at the surface of the body, and approaches an upper limit $P_c$ at a distance $X_c$ from the body 640. Initially, $X_c$ equals $g_1$. However, in some embodiments, $X_c$ changes as a function of time (as particles are deposited).

These mechanisms result in particle deposition to the collection surface of the cylindrical chamber 570. The quantity of particle deposited depends on a great number of parameters, including the particle size distribution, the temperatures $t_C$, $t_H$, and $t_{in}$, and the distance $g_I$.

Typically, the deposition of particles to the collection surface eventually begins to lessen the efficiency of heat transfer between the surface and the gas-particle mixture, and thus to decrease the thermophoretic effect. In preferred embodiments, deposition stops prior to this effect resulting in negative particle characteristics.

Following deposition, the collection phase occurs. During collection phase, the internal cylindrical body 585 is rotated relative to the main body. Rotation of the body 585 is accomplished via the actuator 589, which is coupled with the main body 585, preferably via the drive shaft 587.

During rotation, the scraper 565 dislodges accumulated particulate from the collection surface of the cylindrical chamber 570. The dislodged particulate falls under force of gravity into the consolidation outlet chamber 530. In some embodiments, the dislodged particulate accumulates within the consolidation outlet chamber 530 prior to moving through the chamber and into the consolidation outlet conduit 2. In other embodiments, the dislodged particulate moves through the chamber 530 and into the consolidation outlet conduit 2 in a substantially continuous process.

Typically, the accumulated and dislodged powder is then moved into the consolidation chamber 505 (FIG. 5A) where it is isolated and removed from the collection system. Consolidation as used within this disclosure does not refer to combining particles in a manner that alters their physical characteristics, only to moving a collection of particles together into a common space.

Figure 6:
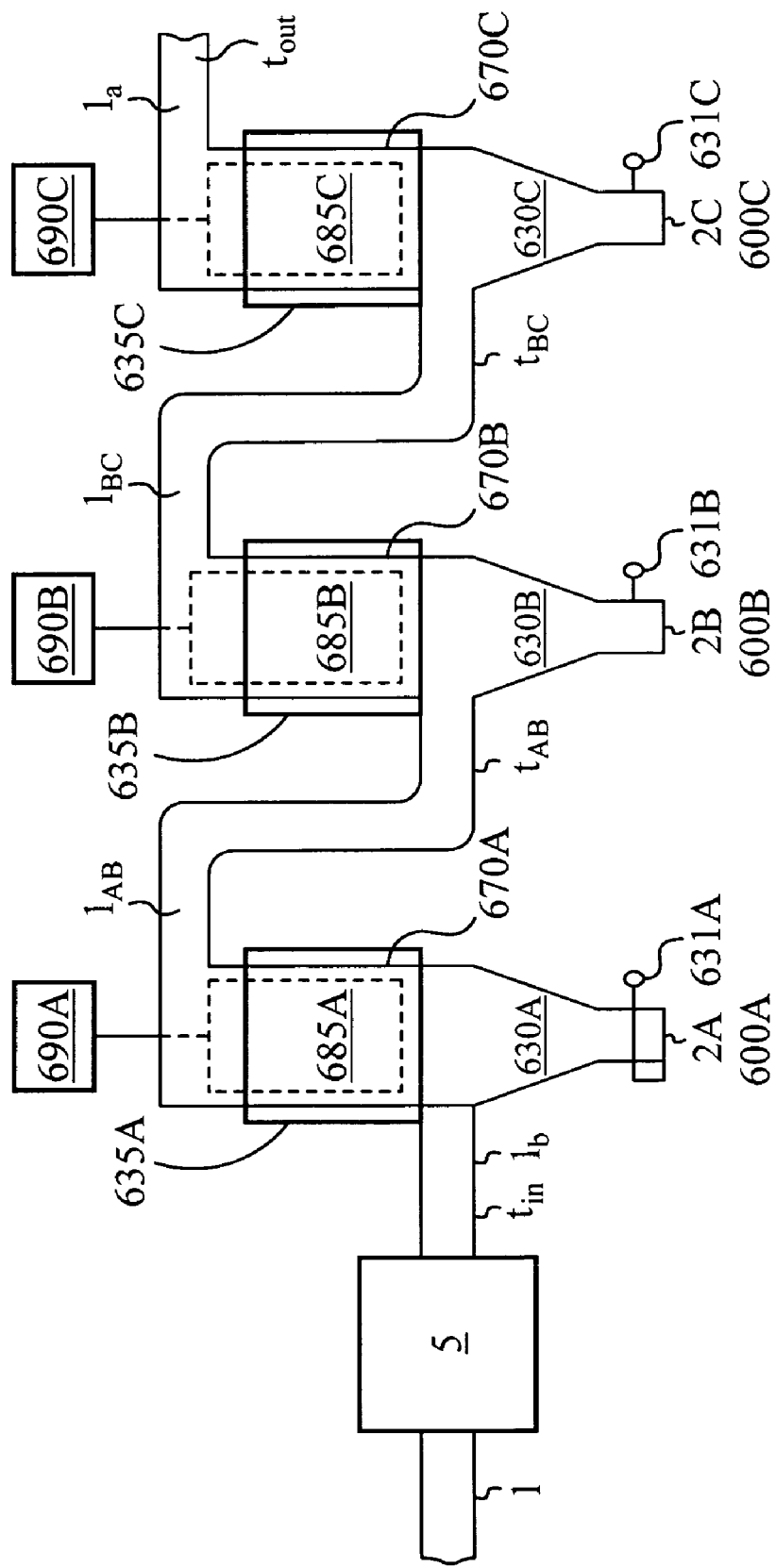
FIG. 6 is a schematic illustration of yet another embodiment of a thermophoretic particle collection system in accordance with the principles of the present invention.

The system 520 of FIG. 5A employs a single collector 500. Other embodiments of the present invention employ multiple collectors within a collection system. For example, FIG. 6 illustrates a collection system that includes a classifier 5 and three collectors, 600A, 600B, and 600C. The system is coupled to the conduit section 1, receives a gas-particle mixture from that section, processes the mixture, and provides the remainder of the mixture as an output to conduit section 1a.

Each collector is configured similarly to the single collector 500 described above. Specifically, the first collector 600A includes a main body consisting of the cylindrical chamber 670A, the consolidation outlet chamber 630A, and an upper collection chamber. The main body is coupled to the conduit section 1AB through the upper collection chamber. Furthermore, the main body is coupled to the conduit section 1b. Additionally, the main body is sealably coupled to the consolidation output conduit 2A. The valve 631A permits sealing of the coupling between the body and the consolidation output conduit 2A.

The internal cylindrical body 685A is disposed within the main body of the collector 600A. The internal cylindrical body 685A is rotatably coupled to the main body of the collector 600A. Preferably, a scraper (not shown) is disposed on the internal cylindrical body 685A and is configured to remove material from the inner surface of the cylindrical chamber 670A during rotation of the internal cylindrical body 685A. The rotation controller 690A is coupled to the internal cylindrical body 685A and configured to actuate and control rotation of the body 685A relative to the main body.

The internal cylindrical body 685A and the internal surface of the cylindrical chamber 670A form a fluid channeling structure coupling the upper collection chamber with the consolidation output chamber 630A.

The collector 600A further comprises the fluid circulation structure 635A, which is preferably coupled to a coolant circulation and heat rejection system (not shown). The fluid circulation structure 635A is configured to circulate fluid in thermal contact with the main body, specifically the cylindrical chamber 670A.

The second collector 600B includes a main body consisting of the cylindrical chamber 670B, the consolidation outlet chamber 630B, and an upper collection chamber. The main body is coupled to the conduit section 1BC, through the upper collection chamber. Furthermore, the main body is coupled to the conduit section 1AB. Additionally, the main body is sealably coupled to the consolidation output conduit 2B. The valve 631B permits sealing of the coupling between the body and the consolidation output conduit 2B.

The internal cylindrical body 685B is disposed within the main body of the collector 600B. The internal cylindrical body 685B is rotatably coupled to the main body of the collector 600B. Preferably, a scraper (not shown) is disposed on the internal cylindrical body 685B and configured to remove material from the inner surface of the cylindrical chamber 670B during rotation of the internal cylindrical body 685B. The rotation controller 690B is coupled to the internal cylindrical body 685B and is configured to actuate and control rotation of the body 685B relative to the main body.

The internal cylindrical body 685B and the internal surface of the cylindrical chamber 670B form a fluid channeling structure coupling the upper collection chamber with the consolidation output chamber 630B.

The collector 600B further comprises the fluid circulation structure 635B, which is preferably coupled to a coolant circulation and heat rejection system (not shown). The fluid circulation structure 635B is configured to circulate fluid in thermal contact with the main body, specifically the cylindrical chamber 670B.

The third collector 600C includes a main body consisting of the cylindrical chamber 670C, the consolidation outlet chamber 630C, and an upper collection chamber. The main body is coupled to the conduit section 1a, through the upper collection chamber. Further, the main body is coupled to the conduit section 1 BC. Additionally, the main body is sealably coupled to the consolidation output conduit 2C. The valve 631C permits sealing of the coupling between the body and the consolidation output conduit 2C.

The internal cylindrical body 685C is disposed within the main body of the collector 600C. The internal cylindrical body 685C is rotatably coupled to the main body of the collector 600C. Preferably, a scraper (not shown) is disposed on the internal cylindrical body 685C and configured to remove material from the inner surface of the cylindrical chamber 670C during rotation of the internal cylindrical body 685C. The rotation controller 690C is coupled to the internal cylindrical body 685C and is configured to actuate and control rotation of the body 685C relative to the main body.

The internal cylindrical body 685C and the internal surface of the cylindrical chamber 670C form a fluid channeling structure coupling the upper collection chamber with the consolidation output chamber 630C.

The collector 600C further comprises the fluid circulation structure 635C, which is preferably coupled to a coolant circulation and heat rejection system (not shown). The fluid circulation structure 635C is configured to circulate fluid in thermal contact with the main body, specifically the cylindrical chamber 670C.

Each collector receives an input, processes it, and produces an output. In the system shown, the output of one collector is provided as an input to the next. Specifically, the classifier 500 is coupled to the conduit section 1 to receive an input therefrom. Additionally, the classifier 500 is coupled to the conduit section 1b to supply an output thereto. Although the illustrated embodiment includes only a single classifier, some embodiments of the present invention include multiple classifiers.

Within a collection system that includes multiple collectors, the basic operation of each collector is similar to that of the single-collector system discussed above. One difference is that the gas-particle mixture temperature changes as the mixture moves through the various collectors. For example, in the collection system shown in FIG. 6, the gas mixture temperature decreases from $t_{in}$ to $t_{AB}$ after passing through the first collector 600A. The second collector 600B decreases the temperature further to $t_{BC}$, and the third collector 600C decreases the temperature even more to $t_{out}$.

Because thermophoretic collection efficiency depends on the strength of the temperature gradient produced, the collection efficiency varies between the multiple collectors in some embodiments. The characteristics of the particles collected depend upon the collection efficiency of the collector, among other things. In some embodiments varying efficiency collectors are used to collect particles of varying characteristics within separate collectors, using the same gas-particle stream.

However, some embodiments of the present invention include features or methods to account for temperature differences in the gas-particle stream. In some embodiments, different temperatures of coolant are used in different collectors to produce equally strong temperature gradients. In some embodiments, the internal cylindrical body is heated to a temperature that depends on the gas-particle mixture temperature.

Typically, within each collector, the accumulated and dislodged powder is then moved into a consolidation chamber (e.g., 505 of FIG. 5A), where it is isolated and removed from the collection system.

Figure 7:
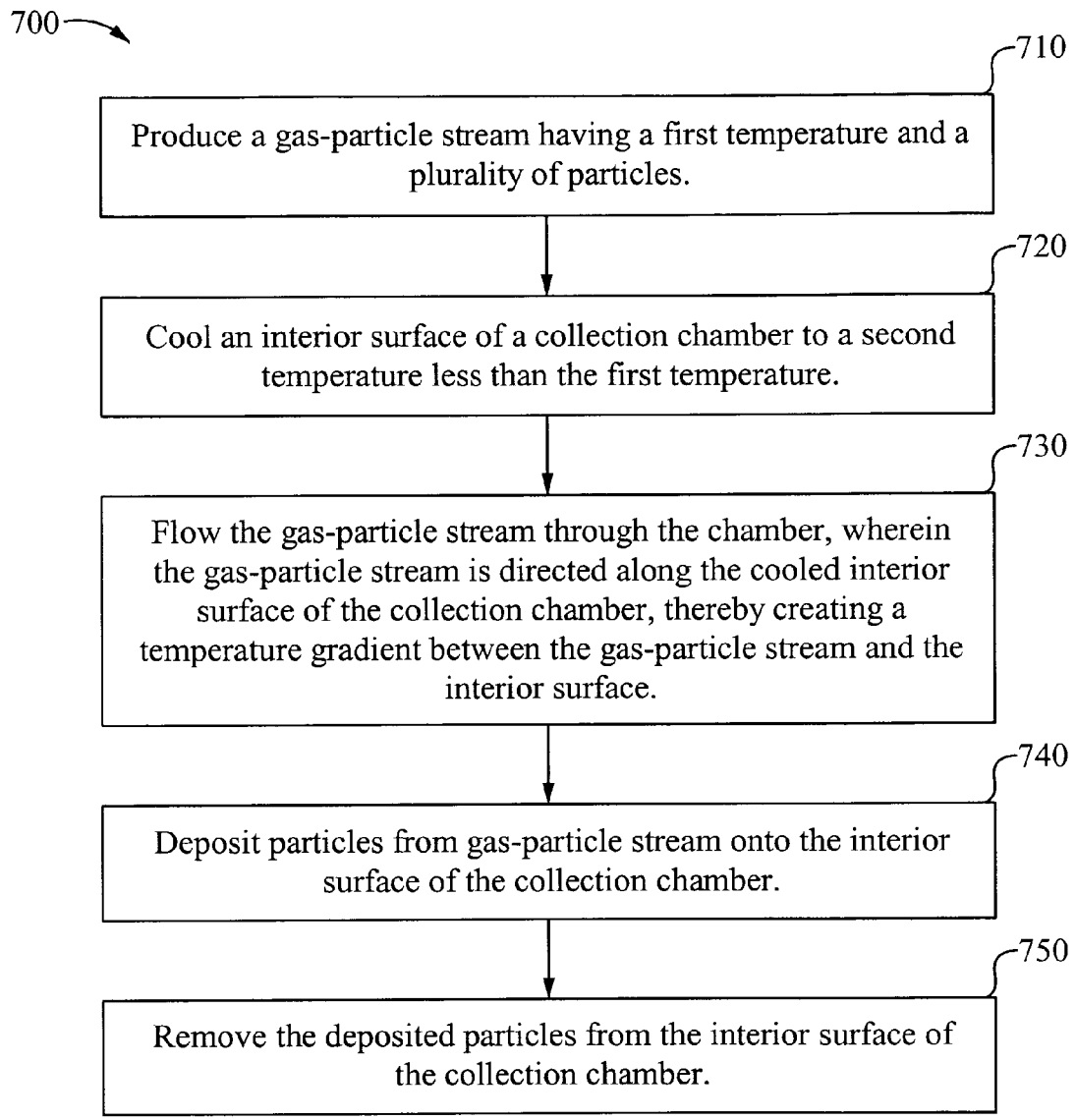
FIG. 7 is a flowchart illustrating one embodiment of a method of collecting particle from a fluid stream in accordance with the principles of the present invention.

FIG. 7 is a flowchart illustrating one embodiment, of a method 700 of purifying powder in accordance with the principles of the present invention. As would be appreciated by those of ordinary skill in the art, the protocols, processes, and procedures described herein may be repeated continuously or as often as necessary to satisfy the needs described herein. Additionally, although the steps of method 700 are shown in a specific order, certain steps may occur simultaneously or in a different order than is illustrated. Accordingly, the method steps of the present invention should not be limited to any particular order unless either explicitly or implicitly stated in the claims.

At step 710, a gas-particle stream is produced. The gas-particle stream has a first temperature and comprises a plurality of particles. It is contemplated that the gas-particle stream can be produced in a variety of ways. However, in a preferred embodiment, the gas-particle stream is produced by energizing a working gas to form a plasma and applying the plasma to powdered material. The powdered material can thereby be vaporized. The vaporized powder can then be conditioned and condensed.

At step 720, the interior surface of a collection chamber is cooled to a second temperature that is less than the first temperature of the gas-particle stream. It is contemplated that the interior surface can be cooled in a variety of ways, including, but not limited to, the techniques discussed above. For example, a coolant circulation system can be used to circulate a fluid in thermal communication with the interior surface.

At step 730, the gas-particle stream flows through the chamber and is directed along the cooled interior surface, thereby creating a temperature gradient between the gas-particle stream and the interior surface. It is contemplated that the gas-particle stream can be directed to the cooled interior surface in a variety of ways, including, but not limited to, the techniques discussed above. For example, the chamber's shape (e.g., larger diameter than opening through which stream enters) can cause the stream to expand and change trajectory, or the chamber can simply restrict the stream's path to a narrow channel adjacent to the interior surface.

At step 740, particles from the gas-particle stream are deposited onto the interior surface of the collection chamber. This deposition is caused by the temperature gradient between the gas-particle stream and the interior surface.

At step 750, the deposited particles can be removed and collected from the interior surface. It is contemplated that the particles can be removed in a variety of ways, including, but not limited to, the techniques discussed above. For example, a rotating scraper can be used to force the deposited particles off of the interior surface and into a container.

The thermophoretic collectors and collection systems of the present invention significantly improve collection of particles from high heat mixtures. To apply traditional filter-based techniques to high heat mixtures, exotic, heat-resistant filters are needed, which increases costs. In the thermophoretic system of the present invention, high heat mixtures provide potentially greater thermophoretic gradients, increasing collection efficiency and decreasing cost.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of collecting particles from a gas-particle stream having
   a first temperature and a plurality of particles, the method comprising:
   cooling an interior surface of a collection chamber to a second temperature less than the first temperature of the gas-particle stream;
   flowing the gas-particle stream through the chamber having an axis, wherein the gas-particle stream is directed along the cooled interior surface of the collection chamber, and a temperature gradient between the gas-particle stream and the cooled interior surface creates a thermophoretic force, wherein the flow of the gas-particle stream has a first velocity vector substantially parallel with the axis and subsequently diverts into a plurality of secondary streams with velocity vectors substantially perpendicular to the axis; and
   the thermophoretic force attracting the particles from the gas-particle stream to the interior surface of the collection chamber, wherein the particles are deposited onto the interior surface of the collection chamber.

2. The method of claim 1, wherein the step of cooling the interior surface comprises circulating coolant to the collection chamber.

3. The method of claim 1, wherein the collection chamber comprises a plurality of circumferential conduits in thermal communication with the interior surface and the step of cooling the interior surface comprises circulating a coolant through the circumferential conduits.

4. The method of claim 1, further comprising the step of producing the gas-particle stream, wherein the step of producing the gas-particle stream comprises energizing a working gas to form plasma and applying the plasma to a powder.

5. The method of claim 1, wherein the collection chamber further has a first end, a second end, and an annular surface positioned a substantially fixed distance
   from the axis, the method further comprising the steps of:
   the collection chamber receiving a gas-particle stream traveling in an axial direction through the first end;
   the collection chamber redirecting the gas-particle stream in a radial direction through a series of radial channels of the annular surface, the annular surface comprising a series of circumferential channels sealed from the collection chamber and configured to permit transport of a fluid therethrough, the radial channels being formed through the annular surface and each radial channel adjacent to at least one circumferential channel; and
   circulating coolant through the series of circumferential channels, thereby cooling the interior surface.

6. The method of claim 1, wherein:
the collection chamber is substantially cylindrical and comprises a plurality of circumferential conduits in thermal communication with the interior surface;
a substantially cylindrical internal body having a smaller radius than the collection chamber is disposed coaxially within the collection chamber, thereby forming an annular channel between the internal body and the interior surface of the collection chamber; and
the step of cooling the interior surface comprises circulating a coolant through the circumferential conduits.

7. The method of claim 6, wherein the step of flowing the gas-particle stream through the chamber comprises the step of flowing the gas-particle stream through the annular channel.

8. The method of claim 7, wherein the internal body comprises scraper, the method further comprising the steps of rotating the internal body and removing the deposited particles from the interior surface with the scraper.

9. The method of claim 8, wherein the scraper is disposed in a helical pattern along the internal body.

10. A thermophoretic particle collector comprising:
a conduit; and
a collection chamber fluidly coupled to the conduit via an inlet and having an interior surface thermally coupled to a fluid circulation structure and a series of radial channels formed through the interior surface, wherein the fluid circulation structure is configured to cool the interior surface to a cooled temperature and the collection chamber is configured to:
receive a gas-particle stream from the conduit via the inlet, the gas-particle stream comprising a plurality of particles and having a temperature greater than the cooled temperature of the interior surface; and
flow the gas-particle stream through the chamber having an axis, wherein the gas-particle stream is directed along the cooled interior surface of the collection chamber, and a temperature gradient between the gas-particle stream and the cooled interior surface creates a thermophoretic force, the thermophoretic force attracting the particles from the gas-particle stream to the interior surface of the collection chamber, wherein the particles are deposited onto the interior surface.

11. The thermophoretic particle collector of claim 10, wherein the collection chamber further has a first end, and a second end, and the interior surface is an annular surface positioned a substantially fixed distance from the axis, the collection chamber being configured to:
receive a gas-particle stream traveling in an axial direction through the first end;
redirect the gas-particle stream in a radial direction through a series of radial channels of the annular surface, the annular surface comprising a series of circumferential channels sealed from the collection chamber and configured to permit transport of a fluid therethrough, the radial channels being formed through the annular surface and each radial channel adjacent to at least one circumferential channel; and
circulate coolant through the series of circumferential channels, thereby cooling the interior surface.

12. The thermophoretic particle collector of claim 10, wherein the collection chamber comprises:
a deceleration chamber having a first end including an inlet, and a second end, wherein the deceleration chamber is configured to receive the gas-particle stream as a primary matter stream having the first velocity vector substantially parallel with the axis through its inlet and divert the primary matter stream into the plurality of secondary matter streams with velocity vectors different from the primary matter stream;
a channeling structure including a plurality of fluid cooling conduits and a narrowed channel, wherein the fluid cooling conduits are separately sealed from the narrowed channel but are in thermal communication with the narrowed channel, the narrowed channel configured to receive the plurality of secondary matter streams from the deceleration structure and transfer the plurality of secondary matter streams through the channeling structure; and
a funneling structure including an outlet, wherein the funneling structure is configured to receive the plurality of secondary matter streams from the channeling structure, join the plurality of secondary matter streams to form an output stream, and deliver the output stream to the outlet of the deceleration chamber;
wherein the fluid circulation structure is a coolant circulation system configured to circulate coolant through the fluid cooling conduits of the channeling structure.

13. The thermophoretic particle collector of claim 10, wherein:
the collection chamber further comprises a channeling structure, the channeling structure having a first end and a second end, the channeling structure forming a channel between a first radially-directed surface positioned a first distance from the axis and a second radially-directed surface positioned a second distance from the axis, the second distance greater than the first distance, the channeling structure configured to receive the gas-particle stream at its first end and channel the gas-particle stream to its second end; and
the fluid circulation structure is a coolant circulation system configured to circulate a coolant in thermal communication with the second radially-directed surface, wherein the second radially-directed surface is the interior surface of the collection chamber.

14. The thermophoretic particle collector of claim 13, wherein the first radially-directed surface is rotatable relative to the second radially-directed surface.

15. The thermophoretic particle collector of claim 14, further comprising a scraper coupled to the first radially-directed surface, wherein the scraper is configured to remove the deposited particles from the second radially-directed surface during rotation of the first radially-directed surface.

16. The thermophoretic particle collector of claim 15, wherein the scraper is helically disposed along the first radially-directed surface.

17. The thermophoretic particle collector of claim 10, wherein the collection chamber is fluidly coupled to a gas-particle production reactor, the gas-particle production reactor configured to:
energize a working gas to form a plasma stream; and
mix a powder into the plasma stream to form the gas-particle stream.

18. The thermophoretic particle collector of claim 10, further comprising a classifier fluidly coupled upstream from the collection chamber, wherein the classifier is configured to receive the gas-particle stream and remove particles from the gas-particle stream that have a mass above a threshold.

19. The thermophoretic particle collector of claim 18, wherein the classifier comprises a classifier conduit having a substantially straight pathway and a curved pathway, the substantially straight pathway leading into a dead end, the curved pathway fluidly coupled to and branching off from the substantially straight pathway upstream from the dead end, wherein the classifier conduit is configured to channel the gas-particle stream through the substantially straight pathway, around and through the curved pathway on the way to the collection chamber, with the particles having a mass above the threshold separating from the gas-particle stream at the curved pathway and flowing into the dead end.

20. A thermophoretic particle collector comprising:
- a deceleration structure having an axis, a first end including an inlet, and a second end, the deceleration chamber configured to receive a primary matter stream having a first velocity vector substantially parallel with its axis through the inlet and divert the stream of matter into a plurality of secondary matter streams with velocity vectors substantially perpendicular to the axis;
- a channeling structure including a plurality of fluid cooling conduits and a matter transfer structure, the fluid cooling conduits separately sealed from the matter transfer structure but in thermal communication with the matter transfer structure, the matter transfer structure configured to receive the plurality of secondary matter streams from the deceleration structure and transfer the plurality of secondary matter streams through the channeling structure;
- a funneling structure including an outlet and being configured to receive the plurality of secondary matter streams from the channeling structure, join the plurality of streams to form an output stream, and deliver the output stream to the outlet; and
- a coolant circulation system configured to circulate coolant through the fluid cooling conduits of the channeling structure.

* * * * *

UNITED STATES PATENT AND TRADEMARK OFFICE
CERTIFICATE OF CORRECTION

| | | |
|---|---|---|
| PATENT NO. | : 7,897,127 B2 | Page 1 of 1 |
| APPLICATION NO. | : 12/151860 | |
| DATED | : March 1, 2011 | |
| INVENTOR(S) | : Frederick P. Layman and Maximilian A. Biberger | |

It is certified that error appears in the above-identified patent and that said Letters Patent is hereby corrected as shown below:

In the Specification
At column 12, line 41, please replace "g," with -- $g_1$ -- so that the corresponding phrase reads
-- spans the distance $g_1$ --.

At column 15, line 15, please replace "520" with -- 520' -- so that the corresponding phrase reads
-- system 520' --.

In the Claims
At column 19, line 52, Claim 11, please replace "a" with -- the -- so that the corresponding phrase
reads -- the series of radial channels --.

Signed and Sealed this
Nineteenth Day of April, 2011

David J. Kappos
*Director of the United States Patent and Trademark Office*